United States Patent
Drovetskaya et al.

(10) Patent No.: US 7,012,048 B2
(45) Date of Patent: Mar. 14, 2006

(54) COMPOSITION AND METHOD FOR TREATING HAIR CONTAINING A CATIONIC AMPHOLYTIC POLYMER AND AN ANIONIC BENEFIT AGENT

(75) Inventors: Tatiana V. Drovetskaya, Basking Ridge, NJ (US); Joseph B. Gardner, Somerset, NJ (US); John S. Thomaides, Berkeley Heights, NJ (US); Lois Dwyer, Bridgewater, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 10/765,667

(22) Filed: Jan. 28, 2004

(65) Prior Publication Data
US 2004/0224862 A1 Nov. 11, 2004

Related U.S. Application Data

(60) Provisional application No. 60/446,667, filed on Feb. 11, 2003.

(51) Int. Cl.
*C11D 1/00* (2006.01)
*C11D 3/28* (2006.01)
*C11D 3/37* (2006.01)

(52) U.S. Cl. .............. 510/123; 510/130; 510/137; 510/138; 510/470; 510/471; 510/475; 510/476; 510/500; 510/504; 510/492; 424/70.11; 424/70.13; 424/70.17; 424/70.22; 424/70.27; 424/70.31

(58) Field of Classification Search ........ 510/119, 510/130, 137, 138, 470, 471, 475, 476, 500, 510/504; 424/70.11, 70.13, 70.17, 70.22, 424/70.27, 70.31
See application file for complete search history.

(56) References Cited

U.S. PATENT DOCUMENTS

| 4,402,977 | A |   | 9/1983  | Grollier et al. |
|-----------|---|---|---------|-----------------|
| 4,590,249 | A |   | 5/1986  | Cabestany et al. |
| 4,943,430 | A | * | 7/1990  | Hefford et al. ............ 424/70.6 |
| 4,994,088 | A |   | 2/1991  | Ando et al. |
| 5,275,809 | A |   | 1/1994  | Chen et al. |
| 5,371,160 | A |   | 12/1994 | Crowe et al. |
| 5,612,024 | A | * | 3/1997  | Giede et al. ............ 424/70.11 |
| 5,776,879 | A |   | 7/1998  | Shih et al. |
| 5,824,756 | A |   | 10/1998 | Scriven et al. |
| 5,929,175 | A |   | 7/1999  | Shih et al. |
| 5,976,516 | A | * | 11/1999 | Sakai et al. ................ 424/70.1 |
| 6,156,829 | A |   | 12/2000 | Shih et al. |
| 6,191,098 | B1|   | 2/2001  | Rodrigues et al. |
| 6,271,386 | B1|   | 8/2001  | Shih et al. |

(Continued)

FOREIGN PATENT DOCUMENTS

EP 0 521 666 1/1993

(Continued)

*Primary Examiner*—Gregory R. Del Cotto
(74) *Attorney, Agent, or Firm*—David P. LeCroy; Karen G. Kaiser

(57) ABSTRACT

The present invention relates to compositions for treating keratin substances, in particular the hair, containing a combination of a cationic ampholytic polymer and an anionic benefit agent as well as to uses thereof. In one embodiment, the composition of the present invention comprises about 0.01 to about 20% by weight of a cationic ampholytic polymer; and about 0.01 to about 20% by weight of an anionic benefit agent.

10 Claims, 6 Drawing Sheets

Representation of polymer structure

U.S. PATENT DOCUMENTS

| | | |
|---|---|---|
| 6,306,815 B1 | 10/2001 | Rodrigues et al. |
| 6,391,995 B1 | 5/2002 | Murugan et al. |
| 6,403,073 B1 | 6/2002 | Cauwet-Martin et al. |
| 6,432,909 B1 | 8/2002 | Srinivas et al. |

FOREIGN PATENT DOCUMENTS

| | | | |
|---|---|---|---|
| EP | 0 869 766 | | 11/2001 |
| FR | 223509 | * | 9/1990 |
| JP | 63 150215 | | 6/1988 |
| JP | 63-150215 | | 6/1988 |
| JP | 01 092211 | | 4/1989 |
| JP | 1-190620 | | 7/1989 |
| JP | 02 223509 | | 9/1990 |
| JP | 04 095017 | | 3/1992 |

\* cited by examiner

Figure 1. Representation of polymer structure

Graph 1. High Humidity Curl Retention

Graph 2

Key: Higher color intensity values correspond to the more pronounced red coloration indicative of more cationic polyampholyte polymer 1 deposited onto the swatch. Intervals that do not overlap indicate significant differences between group averages.

Intervals that do not overlap indicate significant differences between group averages.

Key: Higher color intensity values correspond to the more pronounced red coloration and might be indicative of unremoved cationic material. Intervals that do not overlap indicate significant differences between group averages.

Figure 5 - Picture 1. Hair tresses treated with formulation (5) (labeled "Convenience) versus anti-frizz shampoo controls before combing
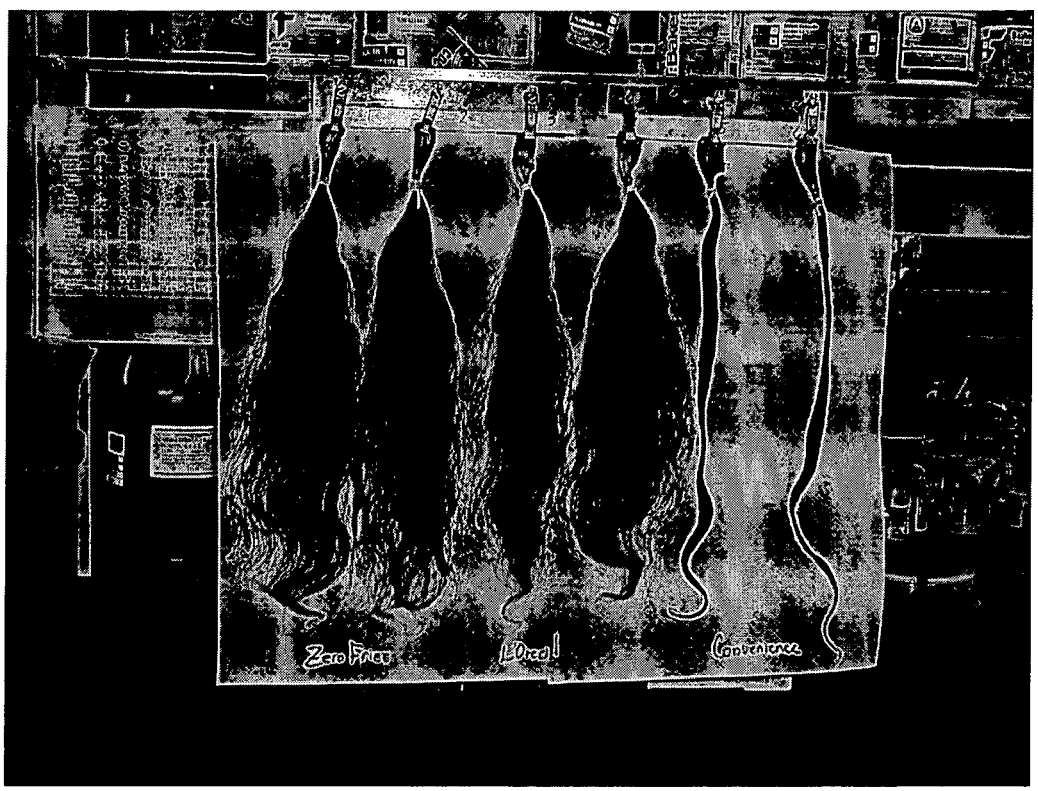

Figure 6 - Picture 2. Hair tresses treated with formulation (5) (labeled "Convenience) versus anti-frizz shampoo controls after being combed 6 times
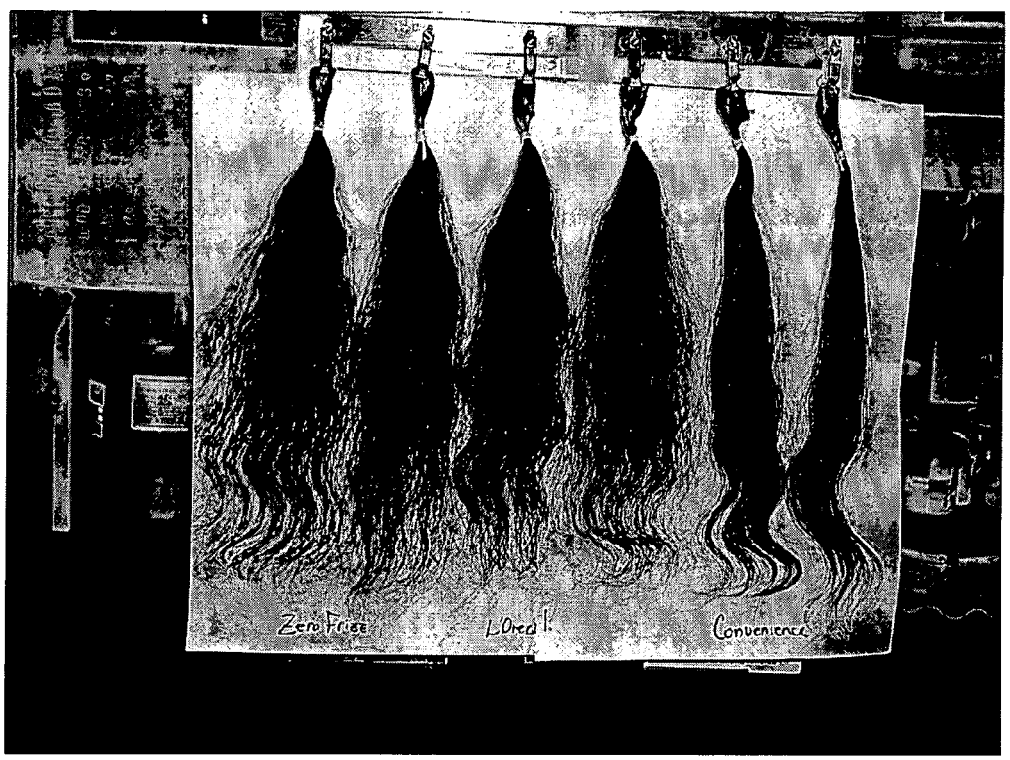

COMPOSITION AND METHOD FOR TREATING HAIR CONTAINING A CATIONIC AMPHOLYTIC POLYMER AND AN ANIONIC BENEFIT AGENT

This application claims priority under 35 USC 119(e) to U.S. Provisional Application No. 60/446,667, filed Feb. 11, 2003.

SUMMARY OF THE INVENTION

The present invention relates to compositions for treating keratin substances, in particular the hair, containing a combination of a cationic ampholytic polymer and an anionic benefit agent as well as to uses thereof.

In one embodiment, the composition of the present invention comprises:
(a) about 0.01 to about 20% by weight of a cationic ampholytic polymer; and
(b) about 0.01 to about 20% by weight of an anionic benefit agent.

In another embodiment, the composition of the present invention further comprises at least one surfactant.

In yet another embodiment, the composition of the present invention further comprises a cosmetically acceptable base.

In one specific embodiment, the ampholytic polymer of the present invention comprises a poly (vinyl pyridine) of formula I:

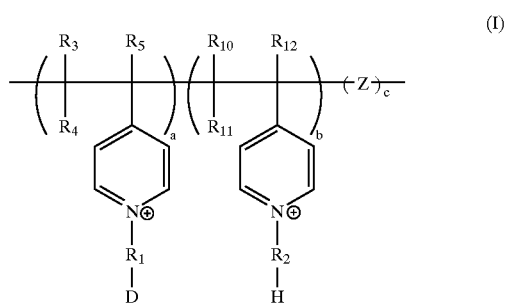

(I)

wherein a represents a mole % of 1 to 99, b represents a mole % of 1 to 99, and c represents a mole % of 0 to 98; $R_1$ is selected from the group consisting of $(CR_6R_7)_{m1}$; $R_2$ is selected from the group consisting of $(CR_8R_9)_{m2}$, benzyl, benzene, and substituted benzene; Z is a residue incorporated into the polymer from an ethylenically unsaturated monomer; $m_1$ and $m_2$ are independently 0 to 20; are each $R_6$, $R_7$, $R_8$, and $R_9$ are independently selected from the group consisting of hydrogen, hydroxyl, alkyl, aryl, or alkaryl and may differ in each repeating unit; and D is selected from groups bearing an anionic charge selected from: $SO_3^-$, $SO_2^-$, $CO_2^-$, $PO_3^-$, and $PO_4^-$; and $R_3$, $R_4$, $R_5$, $R_{10}$, $R_{11}$, and $R_{12}$ are independently H or alkyl.

In yet a further embodiment, the ampholytic polymer of the present invention comprises a copolymer of a betaine containing monomer, a cationic monomer, and, optionally, a neutral monomer represented by formula II:

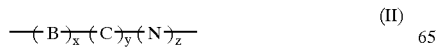

(II)

wherein x represents a mole % of 1 to 99, y represents a mole % of 1 to 99, z represents a mole % of 0 to 98, B represents the residue incorporated into the polymer from an ethylenically unsaturated monomer containing a betaine functionality, C represents the residue incorporated into the polymer from an ethylenically unsaturated monomer containing a cationic charge, and N represents the residue incorporated into the polymer from an ethylenically unsaturated monomer without any charged functionality.

In another embodiment, the composition also includes a benefit agent of xanthan gum.

In yet another embodiment, the present invention is a method of cleaning and styling the hair comprising adding the composition of the present invention and rinsing the hair.

In a further embodiment, the present invention is a method of conditioning and styling the hair comprising adding the composition of the present invention and rinsing the hair.

BACKGROUND OF THE INVENTION

Hair is composed of keratin, a sulfur-containing fibrous protein. The isoelectric point of keratin, and more specifically of hair, is generally in the pH range of 3.2–4.0. Therefore, at the pH of a typical shampoo (about 5.5–6.5), hair carries a net negative charge.

Functional products for hair that provide cleaning and/or additional cosmetic effects after application and rinsing, such as softness, flexibility, good disentangling, a sheen effect and/or a styling effect, have been sought in recent years in the field of hair products.

Amphoteric polymers have been disclosed that provide wet conditioning properties. Many disclosures of amphoteric polymers have been made for a variety of applications and uses. For example, U.S. Pat. Nos. 4,402,977 and 4,996,059 disclose compositions used in the treatment of keratin substances which contain at least one amphoteric polymer.

BRIEF DESCRIPTION OF THE FIGURES

FIG. 5 depicts one example of the frizz-control of the present invention compared with other formulas before being combed.

FIG. 6 depicts one example of the frizz-control of the present invention compared with other formulas after being combed.

DETAILED DESCRIPTION OF THE INVENTION

Figure 1:
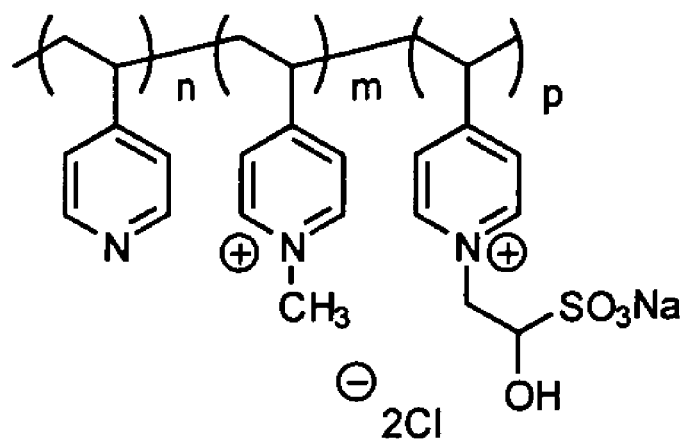
FIG. 1 depicts one embodiment of the structure of the present invention.
Figure 2:
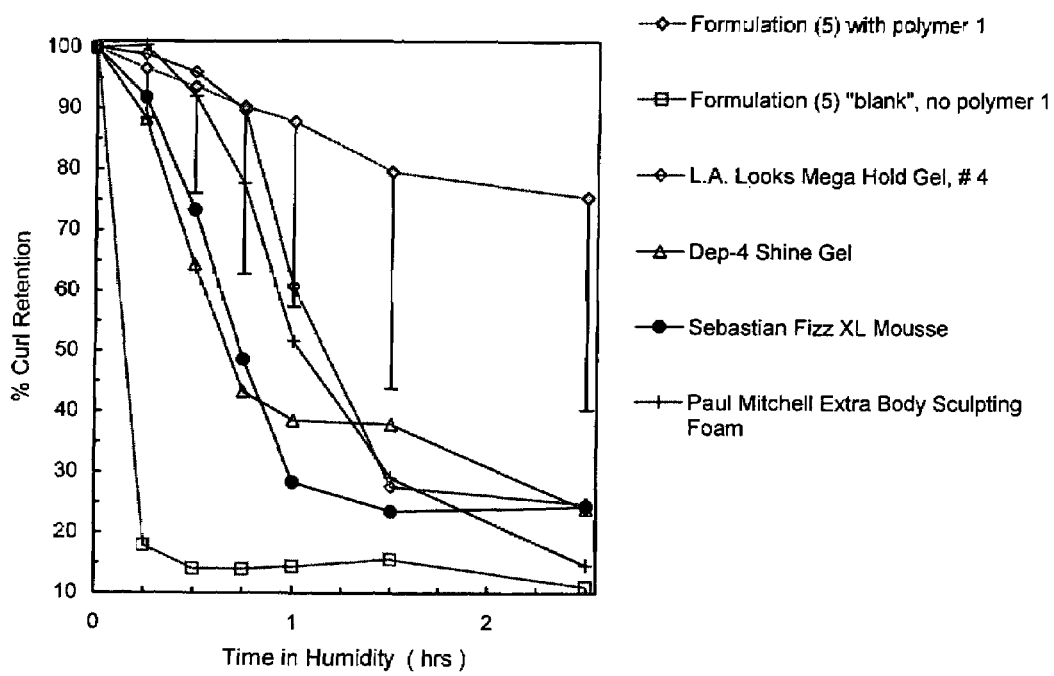
FIG. 2 depicts one example of a high humidity curl retention of the present invention compared with other formulations.
Figure 3:
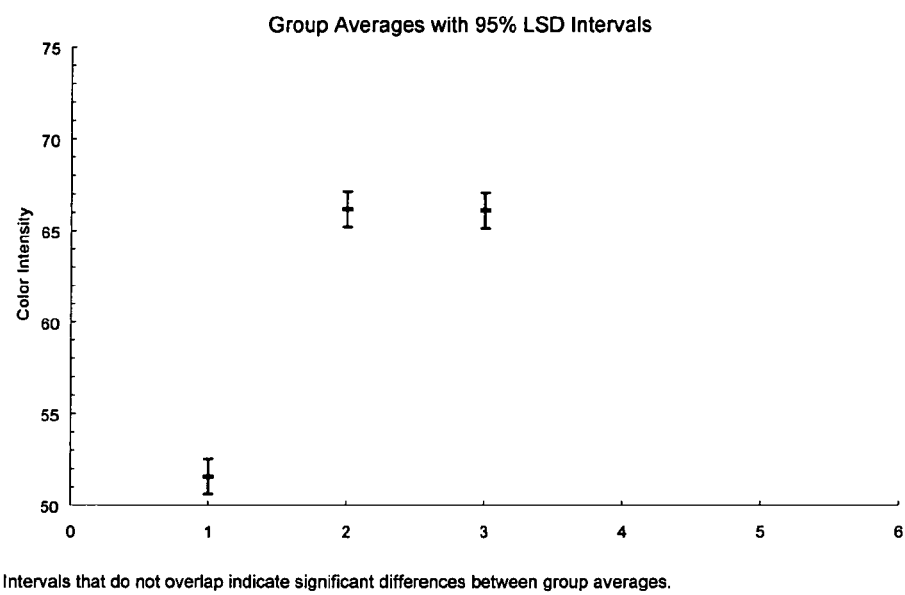
FIG. 3 depicts one example of the color intensity of the present invention compared with other formulations.
Figure 4:
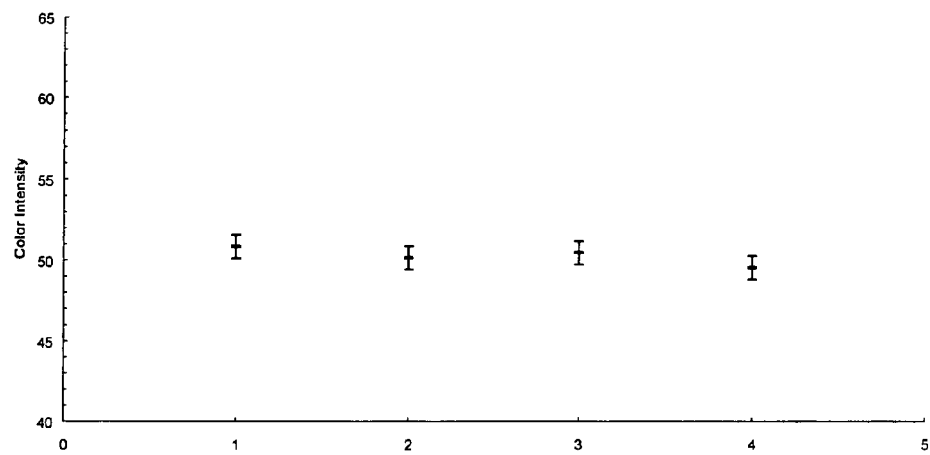
FIG. 4 depicts one example of the color intensity of the present invention compared with other formulations.

In one embodiment, the composition for treating keratin substances, in particular the hair, of the present invention comprises:
(a) about 0.01% to about 20%, by weight, of a cationic ampholytic polymer; and
(b) about 0.01% to about 20%, by weight, of an anionic benefit agent.

In another embodiment, the composition for treating keratin substances, in particular the hair, of the present invention comprises:
(a) about 0.01% to about 20%, by weight, of a cationic ampholytic polymer; and
(b) about 0.01% to about 20%, by weight, of an anionic benefit agent; and
(c) about 0.1% to about 50%, by weight, of a surfactant.

In yet another embodiment, the compositions according to the invention are essentially characterized in that they contain, in a cosmetically and/or dermatologically acceptable aqueous medium, at least:
(a) one cationic ampholytic polymer; and
(b) one anionic benefit agent.

The "cationic ampholytic polymer," in accordance with the invention, has a theoretical net cationic charge of at least about 0.1 meq/g, more specifically, at least about 0.5 meq/g at a pH in the region of about 3–10, more particularly about 5–9. In a more specific example, the net cationic charge is in the range of about 0.5 to about 2.5 meq/g.

Ampholytic polymer, or polyampholyte, as used herein, means a polymer containing both positive and negative charge at a pH in the region of about 3–10, more particularly about 5–9. A cationic ampholytic polymer, or cationic polyampholyte, as used herein, means an ampholytic polymer with a net positive charge. Ampholytic polymers include polymers in which positive and negative charges are present in a single monomer unit or are present in different monomer units.

The ampholytic polymers of the present invention include any cationic ampholytic polymer except polyaminoamide derived polyampholytes. Suitable ampholytic polymers of the present invention include, but are not limited to, poly (vinyl pyridine) derived ampholytes and those arising from the polymerization or copolymerization of ethylenically unsaturated monomers (e.g. acrylates, vinyl acetates, methacrylates, crotonates, acrylamides).

The ampholytic polymers of the present invention can be synthesized by the general methods for preparing polymers including radical, cationic or anionic polymerization, or derivatization of polymers known in the art.

Patent Polymer Description

The cationic polyampholyte can be prepared by means known in the art. In general, the cationic polyampholyte contains cationic and anionic charges, where the number of cationic charges is greater than the number of anionic charges. The polymer may also optionally incorporate neutral monomers.

The cationic charges may come from the incorporation of a cationic monomer into the polymer. Non-limiting examples of suitable cationic monomers include: vinyl N-alkyl pyridinium salts, dimethyldiallylammonium chloride, diallylamine, methyldiallylamine, N,N-dialkyldiallylammonium chloride, dimethylaminoethylmethacrylate, methacryloyloxyethyl trimethylammonium chloride, methacryloyloxyethyl trimethylammonium methyl sulfate, acryloyloxyethyl trimethylammonium chloride, dimethylaminopropylmethacrylamide, methacrylamidopropyl trimethylammonium chloride.

The anionic charges may come from the incorporation of an anionic monomer into the polymer. Non-limiting examples of suitable anionic monomers include: acrylic acid, methacrylic acid, 3-(sulfopropyl)-acrylate potassium salt, 3-(sulfopropyl)-methacrylate potassium salt, 2-acrylamido-2-methylpropanesulfonic acid, crotonic acid, sodium vinyl sulfonate, acrylamidoglycolic acid, 2-acrylamido-2-methylbutanoic acid, 2-acrylamido-2-methylpropanephosphonic acid, sodium vinyl phosphonate, allyl phosphonic acid and salts thereof.

In one specific embodiment, a class of monomers include both positive and negative charges, such as betaines and ylides. Non-limiting examples of suitable betaine monomers include: N-(2-hydroxy-3-sulfopropyl) vinyl pyridinium betaine, N,N-dimethyl-N-(2-methacryloyloxyethyl)-N-(3-sulfopropyl) ammonium betaine, N,N-dimethyl-N-(3-methacrylamidopropyl)-N-(3-sulfopropyl) ammonium betaine, N,N-dimethyl-N-(2-methacryloyloxyethyl)-N-(carboxymethyl) ammonium betaine, and N,N-dimethyl-N-(2-methacryloyloxyethyl)-N-(2-phosphoethyl) ammonium betaine.

In a further embodiment, the polymer may incorporate neutral monomers. Non-limiting examples of neutral monomers include: acrylamides, methacrylamides, acrylates, methacrylates, styrene, and vinyl pyridine.

Alternatively, in another embodiment, the cationic polyampholyte may be prepared by means of polymer modification reactions. A non-limiting example is includes the reaction of a polymer bound basic, nucleophilic amines with alkylating agents including: chloroacetic acid, 1,3-propanesultone, 3-chloro-2-hydroxy-1-propanesulfonic acid sodium salt, 2-chloroethylphosphonic acid, dimethyl sulfate, and alkyl halides.

In accordance with one embodiment of the present invention, the cationic polyampholyte comprises a quaternary nitrogen and an anionic moiety selected from a sulfonate, carboxylate, or phosphonate functionality. For example, in one specific embodiment, the polymer may be represented by the general structure:

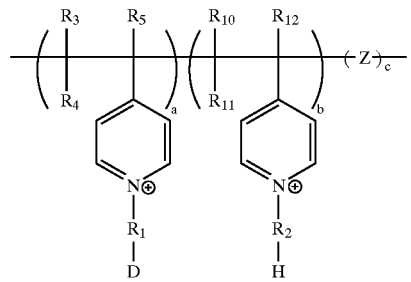

wherein a represents a mole % of 1 to 99, b represents a mole % of of 1 to 99, and c represents a mole % of 0 to 98; $R_1$ is selected from the group consisting of $(CR_6R_7)_{m1}$; $R_2$ is selected from a group consisting of $(CR_8R_9)_{m2}$, benzyl, benzene, and substituted benzene; Z is a residue incorporated into the polymer from an ethylenically unsaturated monomer; $m_1$ and $m_2$ are independently 0 to 20; each of $R_6$, $R_7$, $R_8$, and $R_9$ are independently selected from the group consisting of hydrogen, hydroxyl, alkyl, aryl, or alkaryl and may differ in each repeating unit; and D is selected from groups bearing an anionic charge selected from: $SO_3^-$, $SO_2^-$, $CO_2^-$, $PO_3^-$, and $PO_4^-$; and $R_3$, $R_4$, $R_5$, $R_{10}$, $R_{11}$, and $R_{12}$ are independently H or alkyl.

As used herein, "each of $R_6$, $R_7$, $R_8$, and $R_9$ are independently selected from the group consisting of hydrogen, hydroxyl, alkyl, aryl, or alkaryl and may differ in each repeating unit" means that not only may the four variables differ from each other, but also that they may differ from one repeating unit to the next. For example, $R_1$ may be —CH2—CH(OH)—CH(OH)— when m is 3, $R_6$ is hydrogen in each repeating unit and $R_7$ is hydrogen in the first repeating unit and hydroxyl in the second and third.

In a more specific embodiment of the poly(vinyl pyridine) derivative, a is 5 to 60, b is 5 to 80, and c is 0 to 80; $R_1$ is selected from the group consisting of $(CR_6R_7)_{m1}$; $R_2$ is selected from a group consisting of $(CR_8R_9)_{m2}$; Z is a residue incorporated into the polymer from an ethylenically unsaturated monomer; $m_1$ and $m_2$ are independently 0 to 6; each of $R_6$, $R_7$, $R_8$, and $R_9$ are independently selected from the group consisting of hydrogen, hydroxyl, alkyl, aryl, or alkaryl and may differ in each repeating unit; and D bears an anionic charge selected from the groups: $SO_3^-$, and $CO_2^-$.

The letter Z represents a residue incorporated into the polymer from an ethylenically unsaturated monomer. Suitable ethylenically unsaturated monomers include vinyl pyridine, styrene, substituted vinyl pyridines, substituted styrenes, methacrylates, acrylates, vinyl esters, acrylamides, methacrylamides, crotonoates.

The ethylenically unsaturated monomer is preferentially selected from vinyl pyridine, vinyl imidazolidone, dimethylaminoethylmethacrylate, dimethylaminoethylacrylate, and vinyl pyrrolidone.

In accordance with the invention, yet another embodiment of the ampholytic polymer comprises a copolymer of a betaine containing monomer, a cationic monomer, and, optionally, a neutral monomer. This polymer can be represented by the general structure:

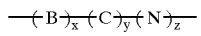

wherein x represents a mole % of 1 to 99, y represents a mole % of 1 to 99, and z represents a mole % of 0 to 98. The symbol B represents the residue incorporated into the polymer from an ethylenically unsaturated monomer containing a betaine functionality, the symbol C represents the residue incorporated into the polymer from an ethylenically unsaturated monomer containing a cationic charge, and the symbol N represents the residue incorporated into the polymer from an ethylenically unsaturated monomer without any charged functionality.

In one embodiment of this structure, x is 2 to 80, y is 2 to 80, and z is 0 to 80. The symbol B represents a monomer selected from the group consisting of N,N-dimethyl-N-(2-methacryloyloxyethyl)-N-(3-sulfopropyl)ammonium betaine, N,N-dimethyl-N-(3-methacrylamidopropyl)-N-(3-sulfopropyl)ammonium betaine, N,N-dimethyl-N-(2-methacryloyloxyethyl)-N-(carboxymethyl)ammonium betaine, N,N-dimethyl-N-(2-methacryloyloxyethyl)-N-(3-sulfo-2-hydroxypropyl)ammonium betaine, and N,N-dimethyl-N-(2-methacryloyloxyethyl)-N-(2-phosphoethyl)ammonium betaine; the symbol C represents a monomer selected from the group consisting of dimethyldiallylammonium chloride, diallylamine, methyldiallylamine, N,N-dialkyldiallylammonium chloride, dimethylaminoethylmethacrylate, methacryloyloxyethyl trimethylammonium chloride, methacryloyloxyethyl trimethylammonium methyl sulfate, acryloyloxyethyl trimethylammonium chloride, dimethylaminopropylmethacrylamide, and [3-(methacryloylamino)propyl]trimethylammonium chloride; and the symbol N represents a monomer selected from the group consisting of acrylamides, methacrylamides, acrylates, methacrylates, and styrene.

The ampholytic polymers of the invention are present in the compositions of the invention in proportions ranging from 0.01 to 20% by weight, more particularly from 0.1 to 10% by weight, most particularly from 0.5 to 5% by weight, relative to the total weight of the composition.

Benefit agents, as used herein, means a material which provides a desirable attribute to the keratin substance, including without limitation, styling, moisturizing, conditioning, shine, volumizing, coloring, protection such as protection from UV and/or oxidants, and anti-frizz or anti-static. Suitable anionic benefit agents of the present invention may include, but are not limited to, anionic polysaccharides. Suitable polysaccharides include, but are not limited to, the following: any of the native or natural polysaccharide polymers obtained from plant, animal and microbial sources. Examples of polysaccharides are modified and natural starches, modified and natural cellulose, anionic gums, and polygalactomannans and derivatives of each. Illustrative examples of suitable anionic polysaccharide benefit agents include gums such as carboxymethylated guar gum, xanthan gum, carboxymethyl cellulose, native or modified potato starch, and oxidized starches.

Suitable anionic benefit agents may also include synthetic anionic polymers and copolymers such as those arising from the polymerization or copolymerization of ethylenically unsaturated monomers (e.g. acrylates, vinyl esters, vinyl ethers, methacrylates, crotonates, maleates, maleic acid, and acrylamides). Illustrative examples include the polymers AMPHOMER® polymeric resin, BALANCE® CR (acrylates copolyer) and FLEXAN® 130 (sodium polystyrene sulfonate) polymers, and RESYN® 28–2930 (vinyl acrylate/crotonates/vinyl deodeconate copolymer) resin.

The anionic benefit agents of the invention are present in the compositions of the invention in proportions ranging from 0.01 to 20% by weight, and more particularly from 0.1 to 10% by weight, relative to the total weight of the composition.

In another embodiment, the aqueous compositions of the invention can also contain inorganic or organic electrolytes that facilitate or allow the ampholytic polymers to be dissolved. Suitable electrolytes include inorganic water-soluble salts such as alkali metal salts, alkaline-earth metal salts or aluminum salts of hydrochloric, sulfuric or nitric acid or of an organic acid such as citric acid, lactic acid or tartaric acid. They can be present in proportions ranging from 0.001 to 30% by weight. Illustrative examples include sodium chloride and ammonium chloride.

The pH of the aqueous compositions in accordance with the invention may be adjusted to between 3–10, and more particularly between 5–9, using base or acid or buffer.

The present composition may also include a surfactant. For example, when the present composition is in the form of a shampoo, in one specific embodiment, the compositions according to the invention may comprise a surfactant base, generally an aqueous one. This surfactant base can also serve to dissolve the ampholyte(s) in the aqueous medium. Suitable surfactant(s) include, but are not limited to, indifferently, alone or as mixtures, from anionic, amphoteric, nonionic, zwitterionic and cationic surfactants.

The minimum amount of surfactant base is that which is just sufficient to give the final composition a satisfactory foaming and/or detergent power and/or to dissolve the polyampholytes present in the composition.

Suitable surfactants which may be used alone or as mixtures include, but are not limited to, the following:
(i) Anionic Surfactant(s):
For example, anionic surfactants, include, without limitation, salts (in particular alkali metal salts, especially sodium salts, ammonium salts, amine salts, amino alcohol salts or magnesium salts) of the following compounds: alkyl sulfates, alkyl ether sulfates, alkyl amidoether sulfates, alkylarylpolyether sulfates, monoglyceride sulfates, alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyl taurates, the alkyl or acyl radical of all of these different compounds may contain from 12 to 20 carbon atoms, and the aryl radical preferably denotes a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; and acyl lactylates in which the acyl radical contains 8 to 20 carbon atoms. It is also possible to use weakly anionic surfactants, such as alkyl D-galactosiduronic acids and their salts, as well as polyoxyalkylenated carboxylic ether acids and their salts, in particular those containing from 2 to 50 ethylene oxide groups, and mixtures thereof. Anionic surfactants also include acylglutamates.

(ii) Nonionic Surfactant(s):

For example, nonionic surfactants include without limitation polyethoxylated, polypropoxylated or polyglycerolated fatty acids, alkylphenols, α-diols or alcohols having a fatty chain containing, for example, 6 to 20 carbon atoms. Mention may also be made of copolymers of ethylene oxide and of propylene oxide, alkanolamides (such as CDEA and LDEA condensates of ethylene oxide and of propylene oxide with fatty alcohols; polyethoxylated fatty amides having from 2 to 30 mol of ethylene oxide, polyglycerolated fatty amides containing on average 1 to 5, and in particular 1.5 to 4, glycerol groups; polyethoxylated fatty amines having 2 to 30 mol of ethylene oxide; oxyethylenated fatty acid esters of sorbitan having from 2 to 30 mol of ethylene oxide; and fatty acid esters of sucrose, fatty acid esters of polyethylene glycol, alkylpolyglucosides, N-alkylglucamine derivatives, amine oxides such as ($C_{10}$–$C_{14}$) alkylamine oxides or N-acylaminopropylmorpholine oxides.

(iii) Amphoteric or Zwitterionic Surfactant(s):

For example, suitable amphoteric or zwitterionic surfactants include (nonlimiting list), aliphatic secondary or tertiary amine derivatives in which the aliphatic radical is a linear or branched chain containing 8 to 18 carbon atoms and containing at least one water-solubilizing anionic group (for example carboxylate, sulfonate, sulfate, phosphate or phosphonate); mention may also be made of carboxybetaines, ($C_8$–$C_{20}$) alkylbetaines, sulfobetaines, ($C_8$–$C_{20}$) alkylamido ($C_1$–$C_6$) alkylbetaines or ($C_8$–$C_{20}$) alkylamido ($C_1$–$C_6$) alkylsulfobetaines. Amphoteric or zwitterionic surfactants would also include amidobetaines and amidosulfobetaines. Zwitterionic surfactants suitable for use in these compositions further include the derivatives of aliphatic quaternary ammonium, phosphonium, and sulfonium compunds, in which the aliphatic radicals are straight or branched, and wherein one of the aliphatic substituents contains from about 8 to 18 carbon atoms and one contains an anionic group, e.g., carboxy, sulfonate, sulfate, phosphate or phosphonate.

(iv) Cationic Surfactants:

Suitable cationic surfactants include without limitation: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

In one embodiment, the surfactant represents from about 0.1 to about 50% by weight of the total weight of the composition.

In another embodiment, the composition of the present invention is a rinse-out product to wash, care for and/or style the hair.

In yet another embodiment, the present invention is a non-therapeutic treatment process for the hair comprising: applying an effective amount of the composition of the present invention directly to the hair and; rinsing the hair with water. In a more specific embodiment, the process further comprises, after applying the composition to the hair, leaving the composition on the hair for a period of time before rinsing the hair with water.

In a further embodiment, the composition comprising the combination of cationic ampholytic polymer and anionic benefit agent of the present invention can improve the properties of various products other than shampoo, such diverse products include detergents including for laundry, hair conditioners, body washes, soap bars, dishwashing compositions, douches, hand and body lotions, suntan lotion, cold creams, preshave and after shave products, deodorant and antiperspirant products in stick, gel, lotion and aerosol foams, cosmetics including lipstick, rouge, mascara and eye liner, facial bases and powders, skin firming compositions, wrinkle and spot removing creams and lotions, and the like, and many other skin and nail care products.

Other materials can be included in such skin and nail care products. Hand and body lotions frequently contain emollients such as stearic acid, glycerol monostearate, mineral oil, glycerine, sesame oil, beeswax, lauryl, myristyl, cetyl and/or stearyl alcohols, lanolin, lecithin, sterols, isopropylmyristate, as well as many other recognized emollients. Emollients are typically used in the compositions of the present invention at levels of from about 1% to about 50% by weight.

The compositions of the present invention optionally contain a nonvolatile, water insoluble, organic, oily liquid as a preferred type of conditioning agent. The conditioning oily liquid can protect, lubricate, and/or moisturize the skin and add shine, softness, and luster to the hair. Additionally, it can also enhance dry combing and dry hair feel. The conditioning oily materials hereof are liquids selected from the group consisting of hydrocarbon oils and fatty esters. The fatty esters hereof are characterized by having at least 12 carbon atoms, and include esters with hydrocarbon chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 19 carbon atoms, although it is not necessarily meant to limit the hydrocarbons to this range. Branched chain hydrocarbon oils can and typically may contain higher numbers of carbon atoms. Also encompassed herein are polymeric hydrocarbons of alkenyl monomers, such as $C_2$–$C_6$ alkenyl monomers.

Specific examples of suitable materials include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and undecane, such as 2,2,4,4,6,6,8,8-dimethyl-10-methylundecane and 2,2,4,4,6,6-dimethyl-8-methylnonane.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyl decyl adipate, lauryl lactate, myristyl lactate, cetyl lactate, oleyl stearate, oleyl oleate, oleyl myristate, lauryl acetate, cetyl propionate, and oleyl adipate.

Di- and tri-alkyl and alkenyl esters of carboxylic acids can also be used. These include, for example, esters of $C_4$–$C_8$ di- and tri-carboxylic acids such as $C_1$–$C_{22}$ esters (preferably $C_1$–$C_6$) of succinic acid, glutaric acid, adipic acid, and citric acid. Specific examples include isocetyl stearyl stearate, diisopropyl adipate, and tristearyl citrate. Polyhydric alcohol esters including alkylene glycol esters and di-fatty acid esters, ethylene glycol mono- and di-fatty acid esters, polyethylene glycol mono and di-fatty acid esters, propylene glycol mono- and di-fatty acid esters, polypropylene glycol mono oleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters are satisfactory for use herein.

Glycerides include mono-, di-, and tri-glycerides. More specifically, included are the mono-, di-, and tri-esters of glycerol and long chain carboxylic acids, such as $C_{10}$–$C_{22}$ carboxylic acids. A variety of these types of materials can be obtained from vegetable and animal fats and oils, such as castor oil, safflower oil, cotton seed oil, corn oil, olive oil, cod liver oil, almond oil, avocado oil, palm oil, sesame oil, lanolin and soybean oil. Synthetic oils include triolein and tristearin glyceryl dilaurate.

In a further embodiment, the compositions of the present invention optionally contain a nonvolatile, nonionic silicone conditioning agent that is insoluble in the compositions hereof. The silicone conditioning agent is intermixed in the composition so as to be in the form of dispersed, insoluble particles, or droplets. The silicone conditioning agent comprises a nonvolatile, insoluble, silicone fluid and optionally comprises a silicone gum, which is insoluble in the composition as a whole but is soluble in the, silicone fluid. The silicone conditioning agent can also comprise other ingredients, such as a silicone resin to enhance deposition efficiency.

In another embodiment, the compositions of the present invention are a liquid that is pourable at room temperature. For example, the compositions can comprise an aqueous carrier, i.e., water, which will generally be present at a level of about 20% to about 95% by weight of the composition, more specifically from about 60% to about 85% for pourable, liquid formulations such as shampoos, shower gels, liquid hand-soaps, and lotions. The compositions of the present invention can also be in other forms, such as gels, mousse, etc. In such cases, appropriate components known in the art such as gelling agents (e.g., hydroxyethyl cellulose), etc. can be included in the compositions. Gels will typically contain from about 20% to about 90% water. Mousses will be a low viscosity composition and will be packaged as a sprayable liquid according to techniques well known in the art, typically in an aerosol canister including a propellant or a means for generating an aerosol spray.

In yet another embodiment, the present compositions may also comprise a variety non-essential, optional components suitable for rendering such compositions more cosmetically or aesthetically acceptable or to provide them with additional usage benefits. A variety of such are known to those skilled in the art in hair, skin and nail care. These ingredients are well-known and include without limiting the invention thereto: pearlescent aids, such as coated mica, ethylene glycol distearate; opacifiers, such as titanium dioxide; preservatives, such as 1,2-dibromo-2,4-dicyano butane (MER-GUARD, Calgon Corporation, Pittsburgh, Pa., USA), benzyl alcohol, 1,3-bis(hydroxymethyl)-5; 5-dimethyl-2,3-imidazolidinedione (e.g., GLYDANT, Lonza Inc., Fairlawn, N.J., USA), methylchloroisothiazolinone (e.g., KATHON, Rohm & Haas Co., Philadelphia, Pa., USA), methyl paraben, propyl paraben, and imidazolidinyl urea; fatty alcohols, such as lauryl alcohol, cetyl alcohol, and stearyl alcohol; sodium chloride; ammonium chloride; sodium sulfate; ethyl alcohol; pH adjusting aids, such as citric acid, sodium citrate, succinic acid, phosphoric acid, monosodium phosphate, disodium phosphate, sodium hydroxide, and sodium carbonate; coloring agents or dyes; perfumes; and sequestering agents, such as disodium ethylenediamine tetra-acetate (EDTA).

Another optional ingredient that can be advantageously used is an anti-static agent. The anti-static agent should not unduly interfere with the in-use performance and end-benefits of the composition. This is more important for shampoo compositions and, the anti-static agent should particularly not interfere with the anionic detersive surfactant. Suitable anti-static agents include, for example, tricetyl methyl ammonium chloride and sulfonated polystyrene.

Typically, from about 0.1% to about 5%; of such anti-static agent is incorporated into the shampoo compositions.

Though the polymer components may act to thicken the present compositions to some degree, the present compositions may also optionally contain other thickeners and viscosity modifiers such as an ethanolamide of a long chain fatty acid, such as polyethylene (3) glycol lauramide and coconut monoethanolamide (cocamide MEA), ammonium xylene sulfonate, polyethylene glycol, and/or hydroxyethyl cellulose.

These optional components generally are used individually in the compositions of the present invention at a level of from about 0.01% to about 10%.

These compositions can be in the form of relatively thickened liquids, creams or gels and they are mainly suitable for washing, caring for and/or styling the hair. They can also be in the form of rinse-out lotions.

As indicated above, the compositions according to the invention give the hair, after rinsing, a noteworthy styling effect which is manifested in particular by an ease of styling and of style maintenance.

The compositions of the present invention are utilized conventionally, i.e., the hair or skin is shampooed or washed by applying an effective amount of the composition to the scalp or skin, and then the hair is rinsed with water. Application of the shampoo to the scalp in general, encompasses massaging or working the shampoo in the hair such that all or most of the hair on the scalp is contacted. The term an "effective amount" as used herein, is an amount that is effective in cleaning and/or conditioning the keratin substrate. Typically, from about 1 g to about 20 g of the composition is applied for cleaning and/or conditioning the hair, and, preferably, the shampoo is applied to hair in a wet or damp state.

The compositions hereof can also be useful for cleaning and conditioning the skin. For such applications, the composition would be applied to the skin in a conventional manner, such as by rubbing or massaging the skin with the composition, optionally in the presence of water, and then rinsing it away with water. In the case of non-rinse-off products, the composition is left in full concentration in contact with the skin.

The following examples illustrate the present invention. It will be appreciated that other modifications of the present invention within the skill of those in the hair, skin or nail care formulation art can be undertaken without departing from the spirit and scope of this invention.

All percentages are calculated by weight of the total composition unless otherwise specifically indicated. All ratios are weight ratios unless otherwise specifically indicated.

EXAMPLES

Synthesis Example of Polymers 1 through 7:

The following example illustrates an embodiment of preparing the functionalized poly(vinyl pyridine) polymers according to the following 2-step procedure. The composition of the final products was controlled through two variables in the reaction sequence: T (time of methylation) and C [amount of CHiPS (3-chloro-2-hydroxy-1-propane sulfonic acid sodium salt) added in the second step]. Decreasing T gives a lower cationic functionality, and decreasing C gives lower betaine functionality. The specific detailed experimental shown below is for Polymer 1.

a) Methylation:

Poly(vinyl pyridine) [Reilline 410 from Reilly Industries, 100 g, 40% solids in a water/methanol solvent system) was added to a Parr shaker high-pressure vessel. The vessel was then charged with a solvent mixture (1:1 v/v water: methanol, 100 g) to dilute the polymer mixture and the solution mixed. The vessel was then connected to the pressure shaker, and the vessel alternately charged with methyl chloride, and depressurized (0.7–1.4 bar (gauge), five times) to saturate the headspace with methyl chloride. The pressure was then raised to 2.4 bar (gauge) with methyl chloride and the reaction mixed for 6 hours (T) at 25° C. (the pressure of the MeCl was kept at 2–2.4 bar gauge over the course of the reaction). After the reaction, the vessel was depressurized and degassed by bubbling nitrogen through the solution. This was used without additional manipulations in the next step (brown solution, 26% solids).

b) Alkylation:

The previously prepared polymer (see above 87 g, 26% solids) was charged to a 4 neck flask fitted with mechanical stirring, an addition funnel, a Dean-Stark trap, and an internal thermometer. The addition funnel was charged with CHiPS (3-chloro-2-hydroxy-1-propane sulfonic acid sodium salt, 13 grams) (C) dissolved in water (50 g). The temperature of the reaction was raised until distillate began to collect in the Dean-Stark trap (reaction temperature ~70° C.). The addition funnel was opened, and the CHiPS solution was added at a rate that was approximately equal to the rate at which the distillate was collected in the trap. The internal temperature rose to 100.5° C. over the course of an hour, at which time the addition finished. The temperature was held steady at 100–102° C. overnight. After 18 hours, the reaction was cooled and delivered for use (brown solution, 38% solids).

The product can be delivered to the shampoo as a dry solid following removal of the water, or as a solution in water (typically at concentrations of 20–50% solids).

TABLE 1

Example Poly(Vinyl Pyridine) polymers

| Sample ID | Mole % plain (n) | Mole % Cationic (m) | Mole % betaine (p) |
|---|---|---|---|
| Polymer 1 | 15 | 22 | 63 |
| Polymer 2 | 50 | 0 (no methylation) | 50 |
| Polymer 3 | 100 | 0 (no methylation) | 0 (no alkylation step) |
| Polymer 4 | 45 | 55 | 0 (no alkylation step) |

Polymer 1 is an inventive example of a cationic polyampholyte at application pH.
Polymer 2 is a comparative example of a neutral polyampholyte at application pH.
Polymer 3 is a comparative example of a neutral polymer (not a polyampholyte) at application pH.
Polymer 4 is a comparative example of a cationic polymer (not a polyampholyte) at application pH.

Polymer 5: Example of Cationic Polyampholyte Without Poly(vinyl pyridine) Backbone A round bottom flask equipped with an internal temperature probe and reflux condenser was charged with dimethyl acrylamide [DMA] (8.42 g, 85 mmol), 3-(methacryloylamino)propyl trimethylammonium chloride [MAPTAC] (15 g, 50% solution in water, 34 mmol), N,N-dimethyl-N-(2-methacryloyloxyethyl)-N-(3-sulfopropyl) ammonium betaine [SPE] (14.28 g, 51 mmol), and water (250 g). The reaction mixture was heated to 80° C., and sodium persulfate was added (400 mg dissolved in 10 mL water). The reaction showed an exotherm, and room temperature water (~100 mL) was slowly added to the reaction mixture to keep the temperature below 90° C. The reaction was maintained at 80° C. for three hours, then allowed to cool to room temperature. The reaction product was used without further purification (10.6% solids).

Polymer 6: Example of a Cationic Polyampholyte Without Methylpyridinium Functionality A four-necked flask equipped with a mechanical stirrer, internal temperature probe, dropping funnel, and Dean-Stark trap was charged with poly(vinyl pyridine) (200 g, 40% solids in water: methanol, Reilline 410). The dropping funnel was charged with a premixed solution of CHiPS (3-chloro-2-hydroxy-1-propane sulfonic acid sodium salt, 58 grams) and 3-chloro-1,2-propanediol (10.2 g) dissolved in water (200 g). The flask was heated until distillate began to collect in the trap, and then the dropping funnel was opened to add the solution dropwise. The temperature was maintained in a manner such that the rates of addition from the addition funnel and distillate collection were about the same. When the addition was complete, the flask internal temperature was maintained at 100° C. for 18 hours. After this time, the reaction was cooled, and delivered for testing without further purification.

Polymer 7: Example of a Cationic Polyampholyte with Carboxybetaine Functionality a) Methylation:

Poly(vinyl pyridine) [Reilline 410, 993 g, 40% solids in a water:methanol solvent system) was added to a Parr shaker high-pressure vessel. The vessel was then charged with a solvent mixture (1:1 v/v water: methanol, 990 g) to dilute the polymer mixture and the solution mixed. The vessel was then connected to the pressure shaker, and the vessel alternately charged with methyl chloride, and depressurized (0.7–1.4 bar (gauge), five times) to saturate the headspace with methyl chloride. The pressure was then raised to 2.4 bar (gauge) with methyl chloride and the reaction mixed for 6 hours (T) at 25° C. (the pressure of the MeCl was kept at 2–2.4 bar (gauge) over the course of the reaction). After the reaction, the vessel was depressurized and degassed by bubbling nitrogen through the solution. This was used without additional manipulations in the next step (brown solution, 32% solids).

b) Alkylation:

The previously prepared polymer (see above, 40 g, 32% solids) was charged to a 4-neck flask fitted with mechanical stirring, an addition funnel, a Dean-Stark trap, and an internal thermometer. The addition funnel was charged with chloroacetic acid (3.27 g) dissolved in water (20 g). The temperature of the reaction was raised until distillate began to collect in the Dean-Stark trap (reaction temperature ~70° C.). The addition funnel was opened, and the chloroacetic acid solution was added at a rate that was approximately equal to the rate at which the distillate was collected in the trap. The internal temperature rose to 100.5° C. over the course of an hour, at which time the addition finished. The temperature was held steady at 100–102° C. overnight. After 18 hours, 2 mL of ammonium hydroxide was added, and the reaction was heated for an additional 5 hours. After this time, the reaction was cooled, and the reaction product was used without further purification.

Polymer 8: Example of a Cationic Polyampholyte with a Phosphobetaine Functionality a) Methylation The methylation was performed as described in polymer 7, part a.

b) Alkylation

Polymer 8a (see above 17.9 g, 28.6% solids) was charged to a 2-neck flask fitted with an addition funnel and a Dean-Stark trap. The flask was stirred with a magnetic stir bar and heated with an external oil bath. The addition funnel was charged with 2-chloroethyl phosphonic acid (2.5 g, 90% technical grade) dissolved in water (10 g). The temperature of the external bath was raised until distillate began to collect in the Dean-Stark trap (bath temperature ~100° C.). The addition funnel was opened, and the contents allowed to add over five minutes. The temperature of the external bath was held steady at 110–115° C. overnight. After 24 hours, 2.5 mL of ammonium hydroxide was added, and the reaction was heated for an additional 1 hour. After this time, the reaction was cooled, and the product was used without further purification (brown liquid, 44.9% solids).

The following examples illustrate shampoo compositions of the present invention. When both components, a cationic polyampholytic polymer and an anionic benefit agent, of the invention are present, the exemplified compositions provide cleansing and styling performance in one application. The hair treated with such styling shampoo composition of the invention can be restyled by wetting. While providing a desirable styling benefit, they do not impart unpleasant feel to the hair and do not form an unpleasant build-up as a result of consecutive multiple applications. If so desired, the compositions may be removed from hair by treating with a conventional cleansing shampoo composition.

All parts, percentages and ratios are by weight unless otherwise specified. The definitions and CTFA designations used in the present invention are as follows:

| Ingredient | Supplier | INCI designation |
|---|---|---|
| AMAZE ™ starch fixative | National Starch and Chemical Company. | Corn starch modified |
| AMPHOMER ® polymeric resin | National Starch and Chemical Company. | Octylacrylamide/Acrylates/Butylaminoethyl Methacrylate copolymer |
| Dehyquart A | Cognis Corp. | Cetrimonium Chloride |
| CELQUAT ® H-100 resin | National Starch and Chemical Company | Polyquaternum-4 |
| Cetiol HE | Cognis Corp. | PEG-7 Glyceryl Cocoate |
| Dermol 89 | Alzo International Inc. | Ethylhexyl Isononanoate |
| FLEXAN ® 130 polymer | National Starch and Chemical Company | Sodium Polystyrene Sulfonate |
| Germaben II | ISP | Diazolidinyl Urea, Methylparaben, Propylparaben |
| Glydant Plus Liquid | Lonza Inc. | DMDM Hydantoin, Iodopropynyl Butylcarbamate |
| Keltrol RD | CP Kelco | Xanthan gum |
| Kessco PEG-6000 DS | Stepan Co. | PEG-150 Distearate |
| Miranol C2M-SF | Rhodia Inc. | Disodium Cocoamphodipropionate |
| Monateric CAB-LC | Uniqema | Cocamidopropyl Betaine |
| Plantapon LGC | Cognis Corp. | Lauryl Glucose Carboxylate |
| Plantaren 1200 N | Cognis Corp. | Lauryl Glucoside |
| Plantaren 2000 | Cognis Corp. | Decyl Glucoside |
| Promidium CO | Uniqema | PPG-2 Hydroxyethyl Cocamide |
| RESYN ® 28-2930 resin | National Starch and Chemical Company | VA/Crotonates/Vinyl Neodecanoate copolymer |
| Rhodamox LO | Rhodia Inc. | Lauramine oxide |
| Standamox O1 | Cognis Corp. | Oleamine oxide |
| Standapol EA-3 | Cognis Corp. | Ammonium Laureth Sulfate |

-continued

| Ingredient | Supplier | INCI designation |
|---|---|---|
| STRUCTURE ® XL polymeric thickener | National Starch and Chemical Company | Hydroxypropyl Starch Phosphate |
| Ticalose 6000 | Tic Gums, Inc. | Cellulose gum |
| Tween 20 | Uniqema | Polysorbate 20 |
| Versene NA | Dow Chemical USA | Disodium EDTA |

Method of Preparation #1 (Formulations (1)–(8), (10)–(22))

A suitable vessel equipped with a means for mixing was sequentially charged at ambient temperature with deionized water (DI), sodium chloride, surfactants, and a cationic ampholytic polymer of the invention. The ingredients were mixed to produce a homogeneous solution. Next, a 2% Keltrol RD stock solution (aqueous, preserved with 1.7 pwt Glydant Plus (55%))* was added. The resulting combination of ingredients was mixed for 10–15 minutes. If desired, the pH of the mixture was adjusted at the end.

* If a benefit agent other than xanthan was used, it was pre-dissolved in DI water and then added to the ingredient mixture as indicated above. If AMPHOMER® polymer or RESYN®28–2930 resin were used, they were neutralized with AMP (2-amino-2-methyl-1-propanol) to allow the dissolution.

Method of Preparation #2 (Formulation (9))

A suitable vessel equipped with a means for mixing and a means for heating was sequentially charged with deionized water, Plantaren surfactants, and PEG-6000. The ingredients were mixed with heating (up to 70° C.) until homogeneous. Heat was removed and a cationic ampholytic polymer of the invention, sodium chloride, and a 2% Keltrol RD stock solution (aqueous, preserved with 1.7 pwt Glydant Plus (55%)) were added with stirring. Next, the remaining ingredients except the preservative were added. The resulting combination of ingredients was mixed for 10–15 minutes. Glydant Plus preservative was added in at the end when the temperature was below 40° C.

The following formulations were prepared according to the methods set forth above.

TABLE 1

Formulations 1 to 4

| Ingredients | (1), wt. % (as is) | (2), wt. % (as is)[1] | (3), wt. % (as is)[2] | (4), wt. % (as is)[3] |
|---|---|---|---|---|
| Miranol C2M-SF (38.4%) | 8.0 | 8.0 | 8.0 | 8.0 |
| Promidium CO (100%) | 3.0 | 3.0 | 3.0 | 3.0 |
| Rhodamox LO (30.4%) | 14.0 | 14.0 | 14.0 | 14.0 |
| Sodium chloride (100%) | 4.5 | 4.5 | 4.5 | 4.5 |
| Polymer 1 (100%) | 2.0 | 2.0 | — | — |
| Xanthan Gum, 3% stock solution[4] | 20.0 | — | 20.0 | — |
| DI Water | q.s. to 100 | q.s. to 100 | q.s. to 100 | q.s. to 100 |
| Styling/Stiffness | Excellent | None | None | None |
| Hair tress appearance, fluffiness | Visibly styled, no fluffiness | Fluffy, soft | Fluffy, soft | Fluffy, soft |
| Color Intensity Value, avrg. from Pyrazol Dye Test[5] (STD) | 68.8 (0.9) | 70.7 (0.9) | 57.8 (0.3) | 52.5 (0.3) |

[1]A comparison formulation; contained all the ingredients of (1) except xanthan (anionic benefit agent).
[2]A comparison formulation; contained all the ingredients of (1) except cationic polyampholyte polymer 1.
[3]A comparison formulation: contained all the ingredients of (1) except xanthan (anionic benefit agent) and cationic polyampholyte polymer 1.
[4]3% Keltrol RD, 1.7% Glydant Plus Liquid (55%)), DI water.
[5]Color intensity is indicative of cationic polymer deposition onto wool swatches that simulate hair, see section F. Higher numbers for composition (1) and (2) signal deposition of cationic polymer 1.

As can be seen, formulation (1), which contained a combination of the cationic polyampholyte polymer 1 and an anionic benefit agent (xanthan) provided excellent post-shampooing hair styling benefits. Comparative formulations (2)–(4) that lacked one or both of the components specified above did not provide desirable styling benefits.

TABLE 2

Formulations 5 to 14

| Ingredients | (5), wt. % (as is) | (6), wt. % (as is) | (7), wt. % (as is) | (8), wt. % (as is) | (9), wt. % (as is) | (10), wt. % (as is)[1] | (11), wt. % (as is)[2] | (12), wt. % (as is)[3] | (13), wt. % (as is) | (14), wt. % (as is) |
|---|---|---|---|---|---|---|---|---|---|---|
| Miranol C2M-SF (38.4%) | — | 8.0 | — | — | — | 8.0 | 8.0 | 8.0 | — | — |
| Monateric CAB-LC (30%) | 27.0 | — | 27.0 | 27.0 | 4.5 | — | — | — | 27.0 | 27.0 |

TABLE 2-continued

Formulations 5 to 14

| Ingredients | (5), wt. % (as is) | (6), wt. % (as is) | (7), wt. % (as is) | (8), wt. % (as is) | (9), wt. % (as is) | (10), wt. % (as is)[1] | (11), wt. % (as is)[2] | (12), wt. % (as is)[3] | (13), wt. % (as is) | (14), wt. % (as is) |
|---|---|---|---|---|---|---|---|---|---|---|
| Plantaren 1200 (50%) | 8.0 | — | 8.0 | 8.0 | 6.5 | — | — | — | 8.0 | 8.0 |
| Plantaren 2000 (50%) | — | — | — | — | 16.2 | — | — | — | — | — |
| Plantapon LGC (36%) | — | — | — | — | 6.5 | — | — | — | — | — |
| Promidium CO (100%) | — | 3.0 | — | — | — | 3.0 | 3.0 | 3.0 | — | — |
| Rhodamox LO (30.4%) | — | 14.0 | — | — | — | 14.0 | 14.0 | 14.0 | — | — |
| Standamox O1 (50%) | — | — | — | — | 4.2 | — | — | — | — | — |
| Standapol EA-3 (26.3%) | — | — | 7.6 | — | — | — | — | — | — | — |
| Dehyquart A (24%) | — | — | — | — | 1.25 | — | — | — | — | — |
| Cetiol HE (100%) | — | — | — | — | 0.5 | — | — | — | — | — |
| Kessco PEG-6000 DS (100%) | — | — | — | — | 1.3 | — | — | — | — | — |
| Sodium chloride (100%) | 4.5 | 4.5 | 4.5 | 4.5 | 4.5 | 1.5 | 5.5 | 2.0 | 4.5 | 1.1 |
| Ethanol | — | — | — | — | — | — | 4.0 | 8.0 | — | — |
| Polymer 1(100%) | — | — | — | — | — | — | — | — | — | — |
| Polymer 1(31.2%) | 6.1 | — | — | — | — | — | — | — | — | — |
| Polymer 1(24.7%) | — | 8.1 | — | — | 8.1 | — | — | — | — | — |
| Polymer 1(39.5%) | — | — | 5.1 | — | — | — | — | — | — | — |
| Polymer 2(100%) | — | — | — | — | — | — | 2.0 | — | — | — |
| Polymer 4(100%) | — | — | — | — | — | 2.0 | — | — | — | — |
| Polymer 3(100%) | — | — | — | — | — | — | — | 2.0 | — | — |
| Polymer 7(32.2%) | — | — | — | — | — | — | — | — | 6.2 | — |
| Polymer 6(40.1%) | — | — | — | 5.0 | — | — | — | — | — | — |
| Polymer 8(44.9%) | — | — | — | — | — | — | — | — | — | 4.4 |
| Xanthan Gum, 3% stock solution[4] | 33.3 | 20.0 | 33.3 | 33.3 | 20.0 | 20.0 | 20.0 | 20.0 | 33.3 | 33.3 |
| Citric Acid (50%) | — | q.s. to pH 6.9 | — | — | — | q.s. to pH 6.9 | q.s. to pH 6.9 | q.s. to pH 6.8 | — | — |
| Sodium hydroxide (25%) | — | — | — | — | — | — | — | — | q.s. to pH 6.7 | q.s. to pH 7.0 |
| Versene NA | 0.005 | — | — | — | — | — | — | — | — | — |
| DI Water | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 |
| Styling/Stiffness | Excellent | Excellent | Good | Excellent | Very Good | Very Good | Little to none | None | Excellent | Good |
| Hair tress appearance, fluffiness | Visibly styled, no fluffiness | Visibly styled, no fluffiness | Visibly styled, no fluffiness | Visibly styled, no fluffiness | Visibly styled, no fluffiness | Visibly styled, no fluffiness | Somewhat fluffy, soft | Somewhat fluffy, soft | Visibly styled, no fluffiness | Visibly styled, no fluffiness |
| Flake | Little to no flake | Little to no flake | Little to no flake | Little to no flake | Little to no flake | Flakes off the hair | Little to no flake | Little to no flake | Little to no flake | Little to no flake |
| Final pH | 5.7 | 6.9 | 5.7 | 5.9 | 6.9 | 6.9 | 6.9 | 6.8 | 6.7 | 7.0 |

[1] A comparison formulation; contained all the ingredients of (6) except that polymer 4 lacked betaine functionalities. Polymer was not a polyampholyte.
[2] A comparison formulation; contained all the ingredients of (6) except that polymer 2 lacked a net cationic charge. Polymer was overall neutral.
[3] A comparison formulation; contained all the ingredients of (6) except that polymer 3 lacked betaine functionalities and a net cationic charge. Polymer was overall neutral in charge and not a
[4] 3% Keltrol RD, 1.7% Glydant Plus Liquid (55%)), DI water.

Compositions (5)–(9) and (13)–(14) further exemplify formulations of the invention providing good post-shampooing hair styling benefits. Formulations (10)–(12) were included for comparison purposes. As can be seen, formulation (10), which contained Polymer 4, a cationic polymer that was not a polyampholyte, flaked off the hair upon drying. Even though formulation (10) provided a post-shampooing styling benefit, its overall performance was unsatisfactory due to excessive flaking. Comparative formulations (11) and (12), which contained polymers that were not cationic (polymers 2 and 3; in addition, polymer 3 in formulation (12) was not a polyampholyte) did not provide desirable styling benefits.

TABLE 3

Formulations 15 to 22

| Ingredients | (15), wt. % (as is) | (16), wt. % (as is) | (17), wt. % (as is) | (18), wt. % (as is)[1] | (19), wt. % (as is) | (20), wt. % (as is) | (21), wt. % (as is) | (22), wt. % (as is) |
|---|---|---|---|---|---|---|---|---|
| Miranol C2M-SF (38.4%) | 8.0 | 8.0 | 8.0 | 8.0 | 8.0 | 8.0 | 8.0 | 8.0 |
| Promidium CO (100%) | 3.0 | 3.0 | 3.0 | 3.0 | 3.0 | 3.0 | 3.0 | 3.0 |
| Rhodamox LO (30.4%) | 14.0 | 14.0 | 14.0 | 14.0 | 14.0 | 14.0 | 14.0 | 14.0 |
| Standamox O1 (50%) | — | — | — | — | — | — | — | — |
| Standapol EA-3 (26.3%) | — | — | — | — | — | — | — | — |
| Sodium chloride (100%) | 4.5 | 4.5 | 4.5 | 4.5 | 4.5 | 4.5 | 4.0 | 4.5 |
| Ethanol | — | — | — | — | — | — | — | — |

TABLE 3-continued

Formulations 15 to 22

| Ingredients | (15), wt. % (as is) | (16), wt. % (as is) | (17), wt. % (as is) | (18), wt. % (as is)[1] | (19), wt. % (as is) | (20), wt. % (as is) | (21), wt. % (as is) | (22), wt. % (as is) |
|---|---|---|---|---|---|---|---|---|
| Polymer 1 (100%) | 2.0 | 2.0 | — | 2.0 | — | — | — | — |
| Polymer 1 (40.8%) | — | — | 4.9 | — | — | — | — | — |
| Polymer 5 (11%) | — | — | — | — | 18.2 | 18.2 | 18.2 | 18.2 |
| Ticalose 6000 (100%) | 1.0 | — | — | — | — | — | — | — |
| Phosphorylated potato starch, lab sample 12171-138-11[2] (10%) | — | 10.0 | — | — | — | — | — | — |
| Carboxymethylated guar gum[3] (100%) | — | — | 1.0 | — | — | — | — | — |
| Amaze (100%) | — | — | — | 1.0 | — | — | — | — |
| Xanthan Gum, 3% stock solution[4] | — | — | — | — | 20.0 | — | — | — |
| Amphomer (100%) | — | — | — | — | — | 1.0 | — | — |
| Flexan 130 (30%) | — | — | — | — | — | — | 3.3 | — |
| Resyn 28-2930 (100%) | — | — | — | — | — | — | — | 1.0 |
| AMP[5] | — | — | — | — | — | q.s. to neutralize/ solubilize the polymer | — | q.s. to neutralize/ solubilize the polymer |
| Citric Acid (50%) | — | — | — | — | — | — | q.s. to pH 7.6 | — |
| Glydant Plus Liquid (55%) | 0.5 | 0.5 | 0.5 | 0.5 | — | 0.5 | 0.5 | 0.5 |
| DI Water | q.s. to 100 | q.s.to 100 | q.s. to 100 | q.s. to 100 | q.s. to 100 | q.s. to 100 | q.s. to 100 | q.s. to 100 |
| Styling/Stiffness | Excellent | Excellent | Good | None | Very Good | Excellent | Very Good | very Good |
| Hair tress appearance, fluffiness | Visibly styled, no fluffiness | Visibly styled, no fluffiness | Visibly styled, no fluffiness | Fluffy, soft | Visibly styled, no fluffiness | Visibly styled, no fluffiness | Visibly styled, no fluffiness | Visibly styled, no fluffiness |
| Flake | Little to no flake | Little to no flake | Little to no flake | Little to no flake | Little to no flake | Little to no flake | Little to no flake | Little to no flake |

[1]A comparison formulation; contained all the ingredients similar to (15)–(17) except its carbohydrate polymer component lacked anionic charge. Supposed "benefit agent" was overall neutral.
[2]Starch was jet-cooked to ensure complete dispersion. The effectiveness of cooking was verified by microscopy.
[3]Ecopol 11DS from Economy Polymers and Chemicals.
[4]3% Keltrol RD, 1.7% Glydant Plus Liquid (55%)). DI water.
[5]2-Amino-2-methyl-1-propanol.

Compositions (15)–(17) and (19)–(22) further illustrate formulations of the invention exemplifying combinations of different types of cationic polyampholytes and anionic benefit agents that provided excellent post-shampooing hair styling benefits. Formulation (18) was included for comparison purposes. As can be seen, formulation (18), which contained an overall neutral supposed "benefit agent" (AMAZE™ starch fixative), did not provide desirable styling benefits.

The following example illustrates conditioner compositions of the present invention. When both components, a cationic polyampholytic polymer and an anionic benefit agent, of the invention are present, the exemplified composition provides conditioning and styling performance in one application. The hair treated with such styling conditioner compositions of the invention can be restyled by wetting. While providing a desirable styling benefit, they do not impart unpleasant feel to the hair and do not form an unpleasant build-up as a result of consecutive multiple applications. If so desired, the compositions may be removed from hair by treating with a conventional cleansing shampoo composition.

Method of Preparation #3 (Formulation (23)–(26))

A suitable vessel equipped with a means for mixing was charged at ambient temperature with deionized water and Keltrol RD/Celquat H-100. The ingredients were mixed until the polysaccharide was fully hydrated. Structure XL was added next. The ingredients were mixed until homogeneous. Next the pre-mixed ingredients Cetiol HE, Dermol 89, Glycerin, Tween 20, a cationic ampholytic polymer of the invention, and sodium chloride were charged and mixing continued until the ingredients were homogeneous. Euperlan PK 3000 and Germaben II were sequentially charged at the end. The resulting combination of ingredients was mixed for 10–15 minutes. If desired, the pH of the mixture was adjusted at the end with citric acid.

The following formulations were prepared according to the method set forth above.

TABLE 4

Formulations 23 to 26

| Ingredients | (23), wt. % (as is) | (24), wt. % (as is)[1] | (25), wt. % (as is)[2] | (26), wt. % (as is)[3] |
|---|---|---|---|---|
| Keltrol RD (100%) | 0.6 | — | 0.6 | — |
| Celquat H-100 (100%) | — | — | — | 1.0 |
| Structure XL (100%) | 2.5 | 2.5 | 2.5 | 5.0 |

TABLE 4-continued

Formulations 23 to 26

| Ingredients | (23), wt. % (as is) | (24), wt. % (as is)[1] | (25), wt. % (as is)[2] | (26), wt. % (as is)[3] |
|---|---|---|---|---|
| Polymer 1 (40.8%) | 4.9 | 4.9 | — | — |
| Sodium chloride (100%) | 3.6 | 2.5 | — | — |
| Cetiol HE (100%) | 3.0 | 3.0 | 3.0 | 3.0 |
| Dermol 89 | 1.0 | 1.0 | 1.0 | 1.0 |
| Glycerin (100%) | 0.5 | 0.5 | 0.5 | 0.5 |
| Tween 20 (100%) | 0.75 | 0.75 | 0.75 | 0.75 |
| Euperlan PK 3000 (45%) | 2.2 | 2.2 | 2.2 | 2.2 |
| Germaben II (44%) | 1.0 | 1.0 | 1.0 | 1.0 |
| Citric Acid (50%) | q.s. to pH 5.3 | q.s. to pH 5.3 | q.s. to pH 5.3 | q.s. to pH 4.7 |
| DI Water | q.s. to 100 | q.s. to 100 | q.s. to 100 | q.s. to 100 |
| Styling/Stiffness | Good | None | None | None |
| Hair tress appearance, fluffiness | Visibly styled, no fluffiness | Somewhat flufffy | Somewhat flufffy | Somewhat flufffy |
| Final pH | 5.3 | 5.3 | 5.3 | 4.7 |

[1] A comparison formulation; contained all the ingredients of (22) except xanthan (anionic benefit agent).
[2] A comparison formulation; contained all the ingredients of (22) except cationic polyampholyte polymer 1.
[3] A comparison formulation; contained all the ingredients of (22) plus Celquat H-100 and did not contain xanthan (anionic benefit agent) and cationic polyampholyte polymer 1.

As can be seen, formulation (23), which contained a combination of the cationic polyampholyte polymer 1 and an anionic benefit agent (xanthan), provided good post-conditioning hair styling benefits. Comparative formulations (24)–(26), which lacked one or both of the components specified above, did not provide desirable styling benefits.

The following examples illustrate methods of use for the compositions of the present invention.

Shampoo Formulations of the Invention

The styling shampoo compositions of the invention were used in a conventional manner. An effective amount of the composition was applied to hair that had preferably been wetted with water, was worked through the hair such that most or all of the hair was contacted with the composition, and was then rinsed off.

Method of Use #1A Styling Shampoo of the Invention:

1 gram of a shampoo formulation of the invention was applied to a 10 inch, ~4.5 gram swatch of pre-wetted brown European virgin hair. The swatch was rubbed with a circular motion between palms 10 times clockwise and 10 times counter clockwise, and rinsed for 30 seconds under 100° F. tap water. The swatch was then combed to detangle and laid flat on a tray or hung on a board and allowed to air-dry overnight—for subsequent subjective panel evaluation or rolled on a teflon mandrel. The curl was allowed to dry in an oven maintained at 120° F. overnight—for subsequent high humidity curl retention study.

Method of Use #1B, Styling Shampoo of the Invention:

1.5 gram of a shampoo formulation of the invention was applied to a 17 inch, ~5.5 gram swatch of pre-wetted brown Caucasian curly frizzy hair from Brazil. The swatch was rubbed with a circular motion between palms 10 times clockwise and 10 times counter clockwise, and rinsed for 30 seconds under 100° F. tap water. The swatch was then combed to detangle, hung on a board and allowed to air-dry overnight—for subsequent anti-frizz performance evaluation.

Styling Controls

Method of Use #2, Commercial Styling Sprays:

Commercial spray was applied by spraying evenly onto a 10 inch, ~4.5 gram swatch of brown European virgin hair for 2 seconds on the each side of the swatch. The swatch was then combed to detangle and further processed/dried as indicated in the preferred method of use #1.

Method of Use #3, Commercial Styling Gels and Mousses:

0.5 g of a commercial gel/mousse was applied to a 10 inch, ~4.5 gram swatch of pre-wetted brown European virgin hair. The product was worked into the swatch 10 times from top to bottom, reversing the swatch to ensure even deposition. The swatch was then combed to detangle and further processed/dried as indicated in the preferred method of use #1.

Conditioner Formulations of the Invention:

The styling conditioner compositions of the invention were used in a conventional manner. An effective amount of the composition was applied to the hair that had preferably been wetted with water, was worked through the hair such that most or all of the hair was contacted with the composition, and was then rinsed off.

Method of Use #4, Conditioner Compositions of the Invention:

One gram of a conditioner formulation of the invention was applied to a 10 inch, ~4.5 gram swatch of pre-wetted brown European virgin hair. The formulation was worked into the hair with a circular motion for 15 seconds and with a "milking motion" for 45 seconds. The swatch was then rinsed for 30 seconds under 100° F. tap water, combed to detangle, and further processed/dried as indicated in the preferred method of use #1A.

Evaluation of Stiffness and Other Subjective Properties

The following examples illustrate the evaluation of stiffness and other subjective properties of hair treated with compositions of the invention against the commercial styling products: Rave Mega Hold Spray (Chesebrough-Ponds), Dep-4 Shine Gel (Schwarzkopf & DEP, Inc.) and Avon Advanced Techniques Mousse (Avon Cosmetics). For each comparative evaluation, 16 swatches were distributed to four panelists in order for each panelist to evaluate two pairs of swatches, one tress treated with a formulation of the invention versus one styling control in each pair. Subjective properties evaluated included gloss, stiffness, dry comb, flake, and feel.

Data acquired from this method are qualitative and subjective. However, panelists who participated in these blind studies have been trained in the analysis of hair swatches for these properties.

Results of the subjective evaluation are summarized in tables 5–7.

Statistical Data Analysis:

Additionally, the subjective evaluations are statistically analyzed to identify differences at the 90% confidence level.

Key: +the experimental sample was statistically superior to the control (minimum 7 out of 8 times the experimental sample was rated superior);

=the experimental sample showed no statistical difference to the control (2–6 out of 8 times the experimental sample was picked over the control);

the experimental sample was statistically inferior to the control (the experimental sample was picked over the control not more than 1 out of 8 times);

Subjective Evaluation Criteria:

1) Gloss—Swatches were gently felt so as not to break the films. They were visually inspected to choose the one exhibiting more shine/gloss.
2) Stiffness—Swatches were gently handled and "felt" for differences in stiffness. Using two fingers, the middles of the swatches were held in a horizontal position to determine which one bends more than the other. The more rigid one was chosen.
3) Dry comb—Swatches were combed through (5) times each and evaluated for ease of combing. The one that combed more easily was chosen.
4) Flake—Both swatches were visually inspected after combing. The teeth of the comb were checked for flake accumulation. The swatches were held at the bound ends, and a fingernail run down the length of the tresses. After inspection, the one with more flaking was chosen.
5) Feel—Swatches were handled to determine preference. The one that felt silkier/cleaner was chosen.

TABLE 5

Evaluation against Rave Mega Hold Hair Spray

| Formulation | Gloss | Stiffness | Dry Comb | Flake | Feel |
|---|---|---|---|---|---|
| (1) | 5/8 (=) | 7/8 (+) | 7/8 (+) | 1/8 (−)* | 8/8 (+) |

*(−) in this category means that the experimental sample showed less flaking than the control.

The data presented in Table 5 indicate that composition (1) was found statistically superior compared to the Rave Megahold Hair Spray in stiffness, dry comb, feel, and flake (less flaking). Gloss was statistically no different from the control.

TABLE 6

Evaluation against Dep-4 Shine Gel

| Formulation | Gloss | Stiffness | Dry comb | Flake* | Feel |
|---|---|---|---|---|---|
| (5) | 3/8(=) | 5/8(=) | 0/8(−) | 1/8(−) | 4/8(=) |

*(−) in this category means that the experimental sample showed less flaking than the control.

According to the data presented in Table 6, formulation (5) showed statistically no difference in stiffness compared to Dep-4 Shine Gel. In other categories, formulation (5) was statistically no different in gloss and feel and inferior in dry comb. It showed less flaking than the leave-on styling control.

TABLE 7

Evaluation against Avon Advanced Techniques Mousse

| Formulation | Gloss | Stiffness | Dry comb | Flake* | Feel |
|---|---|---|---|---|---|
| (5) | 6/8(=) | 2/8(=) | 4/8(=) | 1/8(−) | 2/8(=) |

*(−) in this category means that the experimental sample showed less flaking than the control.

According to the data presented in Table 7, formulation (5) showed statistically no difference in stiffness compared to Avon Advanced Techniques Mousse. In other categories, formulation (5) was statistically no different in gloss, dry comb and feel. It showed less flaking than the control.

Clearly, the inventive formulations perform in a rinse-off context as well as, or better than, the leave-on commercial styling aid formulations.

Evaluation of High Humidity Curl Retention

High humidity curl retention was measured at 70° F., 90% relative humidity for hair tresses shampooed with formulation (5) and tresses treated with commercial leave-on styling aid products:

L.A. Looks Mega Hold Gel #4 (Los Angeles Research Packaging);

Dep-4 Shine Gel (Schwarzkopf & DEP, Inc.);

Sebastian Fizz XL Mousse (Sebastian International, Inc.);

Paul Mitchell Extra Body Sculpting Mousse (John Paul Mitchell Systems);

and tresses treated with a blank formulation (similar to (5) but without polymer 1 of the invention).

The curls were prepared and dried as indicated above (see the preferred method of use #1A), put on boards facing the operator and placed in a high humidity chamber at 70° F. and 90% relative humidity. The percentage of droop was measured at 0.25 hr, 0.50 hr, 0.75 hr, 1.0 hr, 1.5 hr, and 2.5 hr.

Formulation (5) of the present invention provided curl retention statistically superior at the 95% confidence level compared to "Blank" formulation (5) after 15 min. in the humidity chamber, DEP-4 Shine Gel and Sebastian Fizz XL Mousse after 30 min. in the humidity chamber, Paul Mitchell Extra Body Sculpting Foam after 1 hour in the humidity chamber, L.A. Looks Mega Hold Gel, #4 after 1.5 hour in the humidity chamber.

Evaluation of Pyrazol Dye Deposition/Removability Study

The effects of deposition/build-up of cationic polymer 1 of present invention incorporated into a styling shampoo formulation (5) and its removability were assessed on wool swatches using anionic red pyrazol dye* to highlight the cationic deposition. Wool is similar to human hair in absorptive and charge properties and can be used as an efficient substitute for hair testing. Like hair, wool is anionic in nature.

* Pyrazol Fast Red 7BSW Powder, Sandoz Chemicals Corporation.

Deposition/Build-Up Study:

Wool swatches were shampooed with composition (5) one and ten times**, rinsed-off and dyed with an anionic polyazo sulfonate dye, which is attracted to the cationic polyampholyte polymer 1 of the invention. The intensity of the red color is proportional to the amount of deposited cationic material. It was quantified using Brightimeter Micro S-5 instrument. All tests were run in sets of four swatches. Swatches washed with "blank" formulation (5) without polymer 1 were used as controls.

** Swatches were dried in the oven between multiple washings.

Removability Study:

To check for removability, the wool swatches shampooed with formulation (5) were dried and then washed with Original Prell Shampoo (Prestige Brands International, Inc.). The swatches were then dyed with an anionic polyazo sulfonate dye to highlight any residual cationic material that might not be removed after washing. All tests were run in duplicate. Removability of cationic deposition from 1, 3 and 5 consecutive washings** with styling formulation (5) was assessed. Blank swatches washed with Original Prell Shampoo were used as controls.

Preferred Swatch Treatment Procedure:

1. Pre-wash 3×3 inch wool swatches in 1% solution of sodium laureth sulfate.
2. Wash each swatch with 1 gram of formulation (5) for 1 min.
3. Rinse each swatch for 30 seconds under warm running water.
4. Immediately dye in 0.1% Pyrazol dye solution.
5. Oven-dry on aluminum lined trays.
6. Use the brightness meter (Brightimeter Micro S-5) to record "brightness", 5 readings per swatch.
7. Report the color intensity value, which can be calculated as 100 minus brightness.

TABLE 8

Deposition/Build-up studies. LSD Plot & S Chart for Group Comparisons

| Group Number | Group Name | Color Intensity | | | | | Within Group Statistics | | LSD Interval | |
|---|---|---|---|---|---|---|---|---|---|---|
| | | 1 | 2 | 3 | 4 | n | AVG | Std. Dev. | lower limit | upper limit |
| 1 | Formulation (5) "blank" (no polymer) 1 washing | 52.4 | 53.4 | 49.5 | 51.0 | 4 | 51.56 | 1.672 | 50.60 | 52.52 |
| 2 | Formulation (5) 1 washing | 66.2 | 66.7 | 66.2 | 65.7 | 4 | 66.17 | 0.392 | 65.21 | 67.13 |
| 3 | Formulation (5) 10 washings | 65.7 | 68.1 | 66.0 | 64.6 | 4 | 66.10 | 1.463 | 65.14 | 67.06 |

Pooled within-group Standard Deviation (default) = 1.276 (x = excluded)

According to the data presented in Table 8, formulation (5) containing polymer 1 of the invention (groups 2 and 3) showed high levels of deposition onto the wool swatches compared to the blank control (group 1.)

The color intensity values that correspond to one and 10 washings are statistically no different (LSD intervals overlap). No accumulation of cationic build-up as a result of repetitive styling shampoo applications could be therefore detected.

TABLE 9

Removability studies. LSD Plot & S Chart for Group Comparisons.

| Group Number | Group Name | Cleansing Shampoo | Color Intensity | | | Within Group Statistics | | LSD Interval | |
|---|---|---|---|---|---|---|---|---|---|
| | | | 1 | 2 | n | AVG | Std. Dev. | lower limit | upper limit |
| 1 | Pre-washed with styling formulation (5) 1 time | Prell | 51.1 | 50.6 | 2 | 50.84 | 0.304 | 50.12 | 51.55 |
| 2 | Pre-washed with styling formulation (5) 3 times | Prell | 49.9 | 50.4 | 2 | 50.15 | 0.382 | 49.43 | 50.87 |
| 3 | Pre-washed with styling formulation (5) 5 times | Prell | 50.6 | 50.2 | 2 | 50.43 | 0.297 | 49.71 | 51.15 |
| 4 | Blank | Prell | 49.0 | 50.0 | 2 | 49.52 | 0.742 | 48.80 | 50.23 |

Pooled within-group Standard Deviation (default) = 0.623 (x = excluded)

According to the data presented in Table 9, the final color intensity readings (groups 1–3) after cleansing were statistically no different from the Prell control (group 4). This indicates that the inventive composition was removable and no residual cationic deposit could be detected after washing with a conventional cleansing product, whether this deposit originated from one or multiple applications of styling shampoo formulation (5).

G. Anti-Frizz Performance

Anti-frizz properties of formulation (5) of the invention were subjectively evaluated against commercial shampoo products that claim anti-frizz performance: Zero Frizz Hydrating Shampoo (Advanced Research Laboratories) and L'Oreal Curl Vive Curl Moisture Shampoo (L'Oreal USA).

Virgin Caucasian naturally curly/frizzy hair from Brazil was used for the evaluation. The tresses were prepared and dried as indicated in the preferred method of use #1B. Control shampoo formulations were applied in the same manner. On the next day, a picture of hair swatches treated with formulation (5) and commercial controls was taken. The swatches were examined and then combed six times. After that, the swatches were examined again, and a second picture was taken.

Hair tresses treated with formulation (5) (labeled Convenience) were stiff/styled in contrast to the fluffy hair treated with the anti-frizz shampoo controls.

Hair tresses treated with formulation (5) (labeled Convenience) felt clean and soft. They felt softer, less dry/damaged and less raspy compared to the hair treated with the anti-frizz shampoo controls. Hair swatches treated with formulation (5) were visibly less frizzy than the controls.

H. Cleansing Performance

The cleansing ability of formulation (5) of the invention was subjectively evaluated against a blank formulation: similar to (5) but without polymer 1 of the invention. Ten inch Caucasian virgin hair was used in this study. The tresses were pre-treated with synthetic sebum as indicated below to simulate dirty greasy hair. Synthetic sebum that represented an imitation of average sebum was prepared as described in [1]. For each hair swatch, 0.13 g of synthetic sebum was dispersed in 2 g of warm DI water to facilitate spreading. Sebum was worked into each tress ten times from top to bottom, reversing the tress to ensure even deposition. The hair swatches were then hung on boards and allowed to air-dry overnight prior to washing. This treatment with sebum yielded hair tresses that were greasy, dirty and unpleasant to sight and touch.

On the next day, the tresses were washed with styling shampoo formulation (5) of the invention and, for comparison purposes, with a blank shampoo formulation that consisted of the same ingredients as formulation (5) except for Polymer 1 of the invention. The tresses were washed and dried as indicated in the preferred method of use #1A. Control shampoo formulation was applied in the same manner. After drying the swatches overnight as described in the preferred method of use #1A, the polymer film on swatches washed with formulation (5) was broken. All the hair tresses, samples and controls, were then combed three times so the panelists could not guess which tress had been treated with a styling formulation and which one hadn't. Hair swatches were distributed for a subjective panel evaluation in pairs: one cleaned with formulation (5) versus one cleaned with a blank shampoo formulation.

Both hair swatches in each pair looked and felt clean. The results of the subjective panel evaluation are summarized in Table 10. They revealed no statistical difference between swatches in any subjective category tested, indicating that the presence of Polymer 1 of the invention did not affect the cleansing properties of the shampoo chassis.

TABLE 10

Sebum-treated hair washed with styling shampoo formulation (5) versus hair washed with a blank shampoo formulation (no Polymer 1).

| Formulation | Gloss | Stiffness | Dry comb | Flake | Feel |
|---|---|---|---|---|---|
| (5) | 4/8(=) | 5/8(=) | 5/8(=) | 5/8(=) | 3/8(=) |

The data shows that the hair tresses washed with formulation (5) that contained Polymer 1 of the invention were statistically no different from hair tresses washed with a blank shampoo (no Polymer 1) in any subjective category tested.

What is claimed is:

1. A composition which comprises:
   about 0.01 to about 20% by weight of a cationic ampholytic polymer; and
   about 0.01 to about 20% by weight of an anionic benefit agent,
   wherein the ampholytic polymer comprises a poly(vinyl pyridine) of formula I:

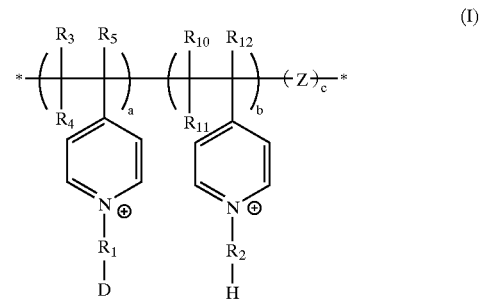

(I)

wherein a represents a mole % of 1 to 99, b represents a mole % of 1 to 99, and c represents a mole % of 0 to 98; $R_1$ is selected from the group consisting of $(CR_6R_7)_{m1}$; $R_2$ is selected from a group consisting of $(CR_8R_9)_{m2}$, benzyl, benzene, and substituted benzene; Z is a residue incorporated into the polymer from an ethylenically unsaturated monomer; $m_1$ and $m_2$ are independently 0 to 20; are each $R_6$, $R_7$, $R_8$, and $R_9$ are independently selected from the group consisting of hydrogen, hydroxyl, alkyl, aryl, or alkaryl and may differ in each repeating unit; and D is selected from groups bearing an anionic charge selected from the group consisting of: $SO_3^-$, $SO_2^-$, $CO_2^-$, $PO_3^-$, and $PO_4^-$; and $R_3$, $R_4$, $R_5$, $R_{10}$, $R_{11}$, and $R_{12}$, are independently H or alkyl.

2. The composition of claim 1, where in the ampholytic polymer further comprises a copolymer of a betaine containing monomer, a cationic monomer, and, optionally, a neutral monomer represented by formula II:

$$*\!-\!\!\overline{(B)}_x\overline{(C)}_y\overline{(N)}_z\!-\!* \qquad (II)$$

wherein x represents a mole % of 1 to 99, y represents a mole % of 1 to 99, z represents a mole % of 0 to 98, B represents the residue incorporated into the polymer from an ethylenically unsaturated monomer containing a betaine functionality, C represents the residue incorporated into the polymer from an ethylenically unsaturated monomer containing a cationic charge, and N represents the residue incorporated into the polymer from an ethylenically unsaturated monomer without any charged functionality.

3. The composition of claim 1, wherein the anionic benefit agent is an anionic polysaccharide.

4. The composition of claim 2, wherein the polysaccharide is selected from the group consisting of modified and natural starches, modified and natural celluloses, anionic gums, and polygalactomannans and derivatives of each.

5. The composition of claim 3, wherein the polysaccharide is selected from the group consisting of carboxymethylated guar gum, xanthan gum, carboxymethyl cellulose, native or modified potato starch, and oxidized starches.

6. The composition of claim 1, wherein the anionic benefit agent is a synthetic anionic polymer or copolymer.

7. The composition of claim 6, wherein the anionic benefit agent is selected from the group consisting of Octylacrylamide/Acrylates/Butylaminoethyl Methacrylate copolymer, acrylates copolymer, sodium polystyrene sulfonate polymers, and vinyl acrylate/crotonates/vinyl deodeconate copolymer.

8. The composition of claim 1, further comprising about 0.1% to about 50% by weight of at least one surfactant.

9. The composition of claim 1, further comprising at least one cosmetically or dermatologically acceptable base.

10. A method of washing, conditioning or styling hair comprising applying an aqueous composition comprising the composition of claim 1 to the hair, and rinsing the hair with water.

* * * * *